(12) United States Patent
Briggs et al.

(10) Patent No.: US 6,507,030 B1
(45) Date of Patent: Jan. 14, 2003

(54) STERLIZATION APPARATUS

(75) Inventors: David Briggs, Reading; Richard Anthony Rudd Little, Freemantle, both of (GB)

(73) Assignee: JenAct Limited, Whitchurch (GB)

( * ) Notice: Subject to any disclaimer, the term of this patent is extended or adjusted under 35 U.S.C. 154(b) by 0 days.

(21) Appl. No.: 09/536,417

(22) Filed: Mar. 28, 2000

Related U.S. Application Data

(63) Continuation of application No. 09/068,849, filed as application No. PCT/GB97/00893 on Mar. 27, 1997.

(30) Foreign Application Priority Data

Mar. 27, 1996 (GB) .............................. 9606438

(51) Int. Cl.7 ................................. A61L 2/10
(52) U.S. Cl. .............................. 250/455.11; 250/504 R; 422/24
(58) Field of Search ................ 422/21, 24; 250/455.11, 250/504 R

(56) References Cited

U.S. PATENT DOCUMENTS 4,001,632 A   1/1977   Haugsjaa et al.
5,166,528 A * 11/1992 Le Vay ..................... 422/24 X
5,614,151 A *  3/1997 Le Vay et al. ................. 422/24

FOREIGN PATENT DOCUMENTS

| EP | 0 357 451 | 3/1990 |
| GB | 2042252 | 9/1980 |
| GB | 2 048 589 | 12/1980 |
| WO | WO89/09068 | 10/1989 |
| WO | WO 96/09842 A1 * | 4/1996 |
| WO | WO96/40298 | 12/1996 |

* cited by examiner

Primary Examiner—Elizabeth McKane
(74) Attorney, Agent, or Firm—Hale and Dorr LLP

(57) ABSTRACT

A sterilizer comprising an openable enclosure (2,4) for surrounding one or more articles (8A, 8B) to be sterilized, the enclosure being arranged to attenuate microwave radiation such that in use, when the enclosure is irradiated with microwave energy, the microwave field energy throughout the interior of the enclosure is significantly less than that outside the enclosure, and the enclosure including a gas tight cavity (2C, 4C) containing a gaseous charge, the charge being chosen from the group of materials which emit ultraviolet radiation when irradiated with microwave radiation.

6 Claims, 2 Drawing Sheets

STERLIZATION APPARATUS

RELATED APPLICATIONS

This is a continuation of U.S. Ser. No. 09/068,849, filed May 19, 1998, now abandoned, which is a continuation of International Patent Application No. PCT/GB97/00893, with an international filing date of Mar. 27, 1996.

BACKGROUND

The present invention relates to sterilisation apparatus.

It is well known that ultraviolet radiation has sterilisation properties. Typically arc lamps are used to produce radiation of an appropriate wavelength. These lamps must be connected to special power supplies and the apparatus is therefore somewhat cumbersome in use. Furthermore, the lamps have a limited life and suffer from shadowing problems caused by their connecting cables and internal electrodes. In the sterilisation field, shadowing can result in parts of an article receiving an insufficient cumulative level of radiation to achieve effective sterilisation.

SUMMARY

It has recently been appreciated that an ultraviolet bulb which is energised by microwave radiation may provide a solution to at least some of the problems associated with arc lamps.

U.S. Pat. No. 5,166,528 describes much of the research performed to date. This patent describes a nonconductive housing which supports one or more microwave energisable ultraviolet bulbs and which is adapted to be placed within the microwave cavity of a conventional microwave oven. An article to be sterilised is placed within the cavity either within or adjacent the housing. In all the described embodiments, the article to be sterilised is exposed to microwave radiation. The patent acknowledges that heating of the article by the microwaves occurs but comments that this is limited because sterilisation only takes 30 to 40 seconds, for example. However, in practice, the applicant has found this to be a significant problem, firstly because any heating of the article may be unacceptable as is the case with some contact lenses, for example, where heating causes distortion of the lens. Secondly, the length of sterilisation needed may be more than 40 seconds, and thirdly, heating of the article is not the only consideration; it is not possible, for example, to sterilise a conductive article using the arrangements described in the patent. Thus, the practical applications of the teaching of U.S. Pat. No. 5,166,528 are limited.

It is an object of the present invention to improve on the teaching of U.S. Pat. No. 5,166,528 and in particular, to solve the problem of sterilisation of microwave sensitive articles using at least one microwave energised ultraviolet bulb.

Accordingly, in a first aspect thereof, the invention provides a steriliser comprising an openable enclosure for surrounding one or more articles to be sterilised, the enclosure being arranged to attenuate microwave radiation such that in use, when the enclosure is irradiated with microwave energy, the microwave field energy throughout the interior of the enclosure is significantly less than that outside the enclosure, and the enclosure including a gas tight cavity containing a gaseous charge, the charge being chosen from the group of materials which emit ultraviolet radiation when irradiated with microwave radiation.

Typically the gaseous charge is of mercury or a metal halide and the enclosure is substantially constructed of an ultraviolet transmissive material such as quartz which is sufficiently heat resistant, microwave transparent and ultraviolet transparent for the purposes of the present invention. By arranging for the enclosure to attenuate the microwave radiation whilst still allowing ultraviolet radiation to penetrate, the disadvantages of the prior art are avoided.

The attenuation may be effected using only the gaseous charge which substantially transforms the incident microwave energy from the microwave to the ultraviolet spectrum by absorbing most of the microwave wavelength and retransmitting the energy in the ultraviolet spectrum. This results in an effective attenuation of microwave energy incident on the article in the enclosure. Alternatively, attenuators such as water (which convert the energy to heat) or electrically conductive elements (arranged to adjust the microwave field in accordance with conventional field theory) may be used. The object of the attenuation is to maximise exposure of the article to ultraviolet radiation at germicidal wavelengths (typically around 260 nm) whilst reducing the microwave energy field to a level insufficient to damage the article or in the case of conductive articles, insufficient to allow arcing and consequent damage to the microwave source.

The preferred embodiment uses only the gaseous charge to attenuate the energy level of the microwave radiation within the enclosure since this results in the most efficient use of the microwave energy (since the energy is largely converted to ultraviolet radiation rather than heat).

According to a second aspect of the invention, a method of sterilising an article comprises placing one or more of the articles into an enclosure, the enclosure including a gas tight cavity containing a gaseous charge, the charge being chosen from the group of materials which emit ultraviolet radiation when irradiated with microwave radiation, and irradiating the enclosure with microwave radiation, the enclosure being arranged such that the energy level of microwave radiation inside the enclosure is less than that outside and is insufficient significantly to damage the article and whereby the article is sterilised by irradiation with ultraviolet radiation.

DESCRIPTION OF DRAWINGS

The invention will now be described by way of example with reference to the drawings in which.

DETAILED DESCRIPTION

Figure 1A:
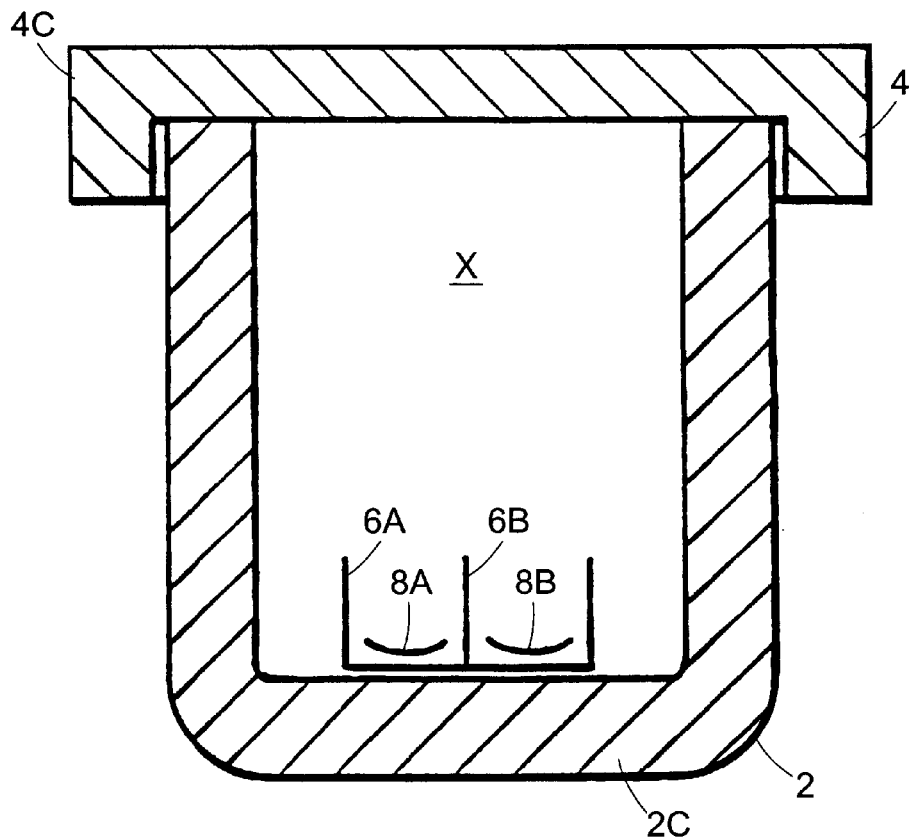
FIG. 1A is cross-section of a steriliser in accordance with the invention, adapted for sterilisation of contact lenses.

With reference to FIG. 1A, the steriliser comprises an enclosure having a base 2 and a lid 4. In plan view, the enclosure is generally circular. The base 2 has two cradles 6A, 6B each for holding a respective contact lens 8A, 8B. The cradles 6 are arranged securely to hold the lenses to prevent them becoming lost and may also be arranged to hold a quantity of fluid such as contact lens soaking solution or saline solution to prevent dehydration of the lenses during sterilisation. The base 2 and lid 4 are hollow to form respective cavities 2C, 4C for holding a gaseous charge which is operable to emit ultraviolet radiation when irradiated with microwave radiation. Typically the charge will be a mercury charge and the lid 4 and base 2 will be constructed from quartz.

In use, the enclosure is placed in a microwave cavity such as a resonant multimode cavity forming part of a conventional microwave oven. Microwave energy is coupled to the cavity in a conventional manner and the substantially even field produced in the cavity causes even irradiation of the outer surface of the enclosure. At least some of the microwave energy is converted to UV energy by the enclosure and the UV energy impinges on an article placed within the enclosure (in this case, a pair of contact lenses).

As a result of the attenuating effect of the gas charge on microwave radiation, the area designated x in the FIG. is substantially free of microwave radiation and thus the lenses 8A, 8B are irradiated substantially only by ultraviolet radiation (and are therefore not 'cooked' by the microwave energy). In a typical arrangement, attenuations of 25 dB of microwave energy are attainable. Whether this is 'significant' attenuation depends on whether it is sufficient to avoid damage to the article (or the microwave source if the article is electrically conductive) given the duration and intensity of the microwave radiation in the interior of the enclosure during sterilisation.

The enclosure of FIG. 1A has external dimensions of approximately 110 mm×150 mm and internal dimensions of approximately 80 mm×120 mm. The gas pressure is low (approximately 1 torr or 1 mmHg) and the charge is of mercury and argon. Higher gas pressures produce greater intensities of UV radiation but heat is also produced in greater quantities which in some applications, may be undesirable.

It will be appreciated that the above described arrangement and those described below may be used for the ultraviolet irradiation of microwave sensitive articles other than contact lenses.

Figure 1B:
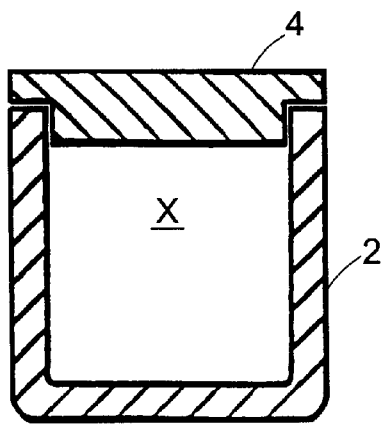
FIG. 1B is a cross-section of an alternative embodiment of FIG. 1A.

With reference to FIG. 1B, an alternative lid configuration is shown in which the central portion of the lid projects downwardly into the base 2. This is an easier shape to manufacture than that of FIG. 1A.

Figure 1C:
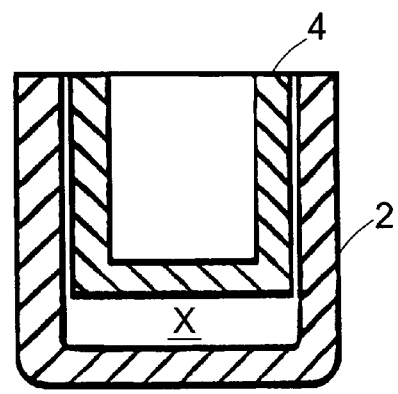
FIG. 1C is a cross-section of an alternative embodiment of FIG. 1A.

With reference to FIG. 1C, the enclosure comprises a lid having a shape similar to that of the base of FIG. A but dimensioned to be placeable concentrically within the base 2. The gap between the sides of the lid 4 and base 2 is dimensioned to have a microwave choke effect in accordance with conventional field theory. This gap will therefore be a function of the microwave wavelength and typically will be a multiple of $\lambda/4$ where $\lambda$ is the wavelength of the microwave radiation.

It will generally be desirable to attenuate the microwave radiation using only the gaseous charge since this results in an efficient conversion of the microwave energy into ultraviolet energy. It may however be necessary to shield certain parts of the articles to be sterilised from ultraviolet radiation or for ease of construction of the enclosure, not to allow the cavities 2C, 4C to entirely surround the enclosure. In this case, other microwave attenuators may be used as shown for example, in FIGS. 1D and 1E.

Figure 1D:
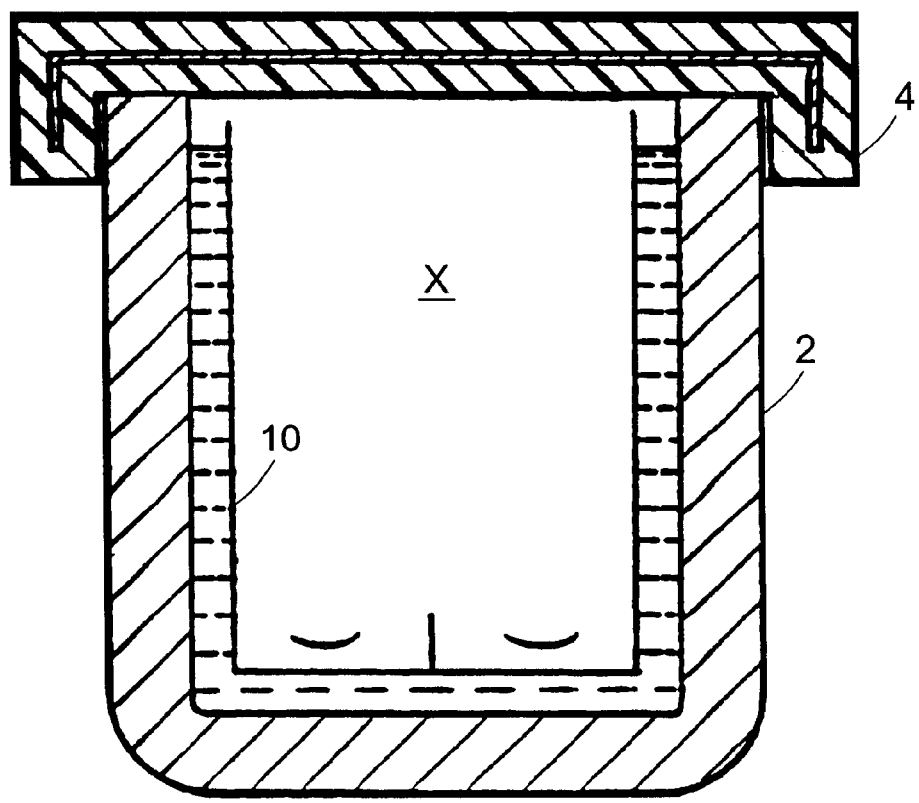
FIG. 1D is a cross-section of an alternative embodiment of FIG. 1A.

In FIG. 1D, a conductive (preferably metallic) lid is used which is encased in PTFE or some other non-conductive material or polymer. This arrangement allows the electromagnetic shielding effect of the conductor to operate without the possibility of arcing to the conductive sides of the microwave cavity in which the steriliser is placed. This embodiment also includes an internal water jacket (which may be used with any of the other embodiments) formed by constructing an inner skin 10 inside the inner surface of the base 2. A water-tight cavity is formed between the inner skin and inner surface into which water may be introduced to form the waterjacket. The purpose of the jacket is further to attenuate the microwave energy as it passes through the enclosure walls. Water is convenient but not essential. Other materials which are largely UV transparent could instead be used for the jacket.

Figure 1E:
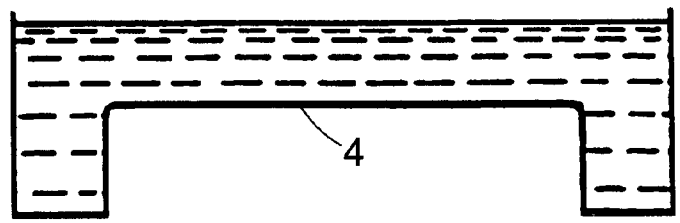
FIG. 1E is an alternative lid for use with the embodiment of FIG. 1D.

FIG. 1E shows an alternative lid which does not include a cavity 4C for a gaseous charge, in which the lid is open at the top allowing it to be filled with water. As discussed above, the water attenuates the microwave energy by converting it to heat energy.

The microwave radiation may also be attenuated using a conductive, reticular material such as a wire mesh, the pitch of reticulation being chosen in relation to the wavelength of the microwave radiation as a compromise between minimising the attenuation of the ultraviolet radiation and maximising that of the microwave radiation.

It should be appreciated that the term 'sterilisation' is used loosely in the sense that the wavelength, intensity and duration of UV irradiation may be adjusted either empirically or using known methods in order to achieve a desired degree of bacterial destruction on the surface of the article or articles in the enclosure. It will also be appreciated that the described apparatus could be used for nonsterilisation applications such as resin and/or ink curing.

Accordingly, other embodiments are within the scope of the following claims.

What is claimed is:

1. A sterilizer comprising a double-walled container and a closure, the container being formed from a material which is generally transmissive to radiation at microwave wavelengths and the space defined between the walls being filled with a gaseous charge which radiates in the ultraviolet spectrum when irradiated with energy at microwave wavelengths, and the closure being arranged to extend at least partly into the container adjacent the inner surface of the container, the dimensions of the container and the extended part of the closure being dimensioned to define a gap between the inner surface of the container and the outer surface of the extended part of the closure which is of predetermined size, the size of the gap being chosen to form a microwave choke arrangement.

2. A sterilizer according to claim 1 wherein the predetermined gap is substantially a multiple of $\lambda/4$ where $\lambda$ is the wavelength of the said microwave radiation.

3. A sterilizer according to claim 1, wherein the closure is double-walled and the space defined between the walls is filled with a gaseous charge which radiates in the ultraviolet spectrum when irradiated with energy at microwave wavelengths.

4. A sterilizer according to claim 1, wherein the closure is formed from an electrically conductive material and is covered with an electrically insulative material.

5. A sterilizer according to claim 1, wherein the closure defines a liquid tight space for containing a microwave-attenuating liquid.

6. A sterilizer according to claim 1, wherein the container includes a third wall within its inner surface which defines with the inner surface of the container, a liquid tight space for containing a microwave-attenuating liquid.

* * * * *